US012778715B2

(12) United States Patent
Al Hezaimi

(10) Patent No.: US 12,778,715 B2
(45) Date of Patent: Nov. 3, 2026

(54) PULP CAPPING METHODS

(71) Applicant: Khalid Al Hezaimi, Newport Beach, CA (US)

(72) Inventor: Khalid Al Hezaimi, Newport Beach, CA (US)

( * ) Notice: Subject to any disclaimer, the term of this patent is extended or adjusted under 35 U.S.C. 154(b) by 382 days.

(21) Appl. No.: 18/393,148

(22) Filed: Dec. 21, 2023

(65) Prior Publication Data

US 2024/0122675 A1 Apr. 18, 2024

Related U.S. Application Data

(63) Continuation of application No. 17/363,827, filed on Jun. 30, 2021, now Pat. No. 11,890,154.

(51) Int. Cl.
*A61C 5/20* (2017.01)
*A61K 6/69* (2020.01)
*A61K 6/851* (2020.01)

(52) U.S. Cl.
CPC .................. *A61C 5/20* (2017.02); *A61K 6/69* (2020.01); *A61K 6/851* (2020.01)

(58) Field of Classification Search
CPC .... A61C 5/20; A61C 5/40; A61C 5/50; A61K 6/69; A61K 6/851
See application file for complete search history.

(56) References Cited

U.S. PATENT DOCUMENTS

| | | | |
|---|---|---|---|
| 4,350,687 | A | 9/1982 | Lipton et al. |
| 4,845,075 | A | 7/1989 | Murray et al. |
| 5,045,633 | A | 9/1991 | Murray et al. |
| 5,073,114 | A | 12/1991 | Detcsh |
| 5,124,316 | A | 6/1992 | Antoniades et al. |
| 5,455,041 | A | 10/1995 | Genco et al. |
| 7,473,678 | B2 | 1/2009 | Lynch |
| 8,029,769 | B2 | 10/2011 | Lyngstadaas et al. |
| 8,636,986 | B2 | 1/2014 | Van Dyke |
| 9,486,393 | B2 | 11/2016 | Jensen |
| 2005/0020720 | A1 | 1/2005 | Dickens et al. |
| 2005/0079470 | A1 | 4/2005 | Rutherford et al. |
| 2007/0009858 | A1 | 1/2007 | Hatton et al. |
| 2008/0318190 | A1 | 12/2008 | Suh et al. |
| 2009/0215009 | A1 | 8/2009 | Noishiki et al. |
| 2009/0258330 | A1 | 10/2009 | Huber et al. |
| 2010/0203481 | A1 | 8/2010 | Murray et al. |
| 2011/0171607 | A1 | 7/2011 | Mao et al. |
| 2011/0182995 | A1 | 7/2011 | Asgary |
| 2012/0156308 | A1 | 6/2012 | Lovschall et al. |
| 2012/0164604 | A1 | 6/2012 | Nakashima et al. |
| 2012/0231422 | A1 | 9/2012 | Naseem et al. |
| 2013/0149667 | A1 | 6/2013 | Lu et al. |
| 2014/0023979 | A1 | 1/2014 | Mounir |

(Continued)

OTHER PUBLICATIONS

Al-Hezaimi et al., 2011, "A hybrid approach to direct pulp capping by using emdogain with a capping material," J. Endod, 37(5):667-672.

(Continued)

*Primary Examiner* — Tracy Vivlemore
*Assistant Examiner* — Thomas R. Amick
(74) *Attorney, Agent, or Firm* — Jones Day

(57) ABSTRACT

Methods of treating exposed tooth pulp are provided herein, including, e.g., methods of pulp capping comprising administering a combination of growth factor substance and pulp capping material to exposed pulp thereby inducing dentin formation and/or pulp revitalization.

17 Claims, 12 Drawing Sheets

(56) References Cited

U.S. PATENT DOCUMENTS

| | | | |
|---|---|---|---|
| 2014/0272803 | A1 | 9/2014 | Nevins |
| 2014/0322672 | A1 | 10/2014 | Nakashima et al. |
| 2016/0045403 | A1 | 2/2016 | White et al. |
| 2018/0116915 | A1 | 5/2018 | Alshwaimi et al. |
| 2018/0263860 | A1 | 9/2018 | Yassen et al. |
| 2019/0142701 | A1 | 5/2019 | Bleier |
| 2019/0247396 | A1 | 8/2019 | Sharpe |
| 2020/0179085 | A1 | 6/2020 | Fakhrzadeh et al. |
| 2020/0289378 | A1 | 9/2020 | Carlson et al. |
| 2020/0306143 | A1 | 10/2020 | Yelick et al. |
| 2020/0405916 | A1 | 12/2020 | Taboas et al. |
| 2021/0077223 | A1 | 3/2021 | Mounir et al. |
| 2021/0386516 | A1 | 12/2021 | Bahammam et al. |
| 2022/0362109 | A1 | 11/2022 | Nakashima et al. |

OTHER PUBLICATIONS

Al-Hezaimi et al., 2011, "Histomorphometric and micro-computed tomography analysis of pulpal response to three different pulp capping materials," J. Endod, 37(4):507-512.

Al-Hezaimi et al., 2020, "Evaluation of Recombinant Human Platelet-Derived Growth Factor or Enamel Matrix Derivative Plus Calcium Hydroxide for Pulp Capping: A Randomized Controlled Human Clinical Trial," Int. J. Periodontics Restorative Dent., 40(5):645-654.

Al-Hezaimi et al., 2020, "Regeneration of Secondary Dentin Using Recombinant Human Platelet-Derived Growth Factor and MTA for Pulp Capping: A Randomized Controlled Human Clinical Trial," Int. J. Periodontics Restorative Dent., 40(4):477-485.

Garrocho-Rangel et al., 2009, "Efficacy of EMD versus calcium hydroxide in direct pulp capping of primary molars: a randomized controlled clinical trial," Oral Surg. Oral Med. Oral Pathol. Oral Radiol. Endod, 107(5):733-738.

GEM21S Growth-Factor Enhanced Matrix product brochure, Lynch Biologics LLC, Year: 2018 (20 pages).

Hilton, 2009, "Keys to clinical success with pulp capping: a review of the literature," Oper Dent., 34(5):615-625.

Kiatwateeratana et al., 2009, "Partial pulpotomy on caries-free teeth using enamel matrix derivative or calcium hydroxide: a randomized controlled trial," Int. Endod J., 42(7):584-592.

Komabayashi et al., 2016, "Current status of direct pulp-capping materials for permanent teeth," Dent. Mater J., 35(1):1-12.

Nevins et al., 2003, "Periodontal regeneration in humans using recombinant human platelet-derived growth factor-BB (rhPDGF-BB) and allogenic bone," J. Periodontol., 74(9):1282-1292.

Zhang et al., 2006, "The performance of human dental pulp stem cells on different three-dimensional scaffold materials," Biomaterials, 27(33):5658-5668.

Zhang et al., 2008, "Hard tissue formation in a porous HA/TCP ceramic scaffold loaded with stromal cells derived from dental pulp and bone marrow, " Tissue Eng. Part A, 14(2): 285-294.

Zhang et al., 2017, "The Effects of Platelet-Derived Growth Factor-BB on Human Dental Pulp Stem Cells Mediated Dentin-Pulp Complex Regeneration," Stem Cells Transl. Med., 6(12):2126-2134.

Anonymous, 2020, "Glossary of Endodontic Terms," American Association of Endodontists Tenth Edition, 48 pages.

Li et al., 2015, "Direct Pulp Capping with Calcium Hydroxide or Mineral Trioxide Aggregate: A Meta Analysis," American Association of Endodontists, 41(9): 1412-1417.

Matsuura et al., 2021, "Long-term clinical and radiographic evaluation of the effectiveness of direct pulp capping materials: A meta-analysis," Dental Materials Journal, 41(1):1-7.

Shenkin et al., 2019, "Mineral Trioxide Aggregate May Be The Most Effective Direct Pulp Capping Material," The Journal of Evidence-Based Dental Practice, 19(2):183-185.

Chu et al., 2010, "Comparison of the microstructure of crown and root dentin by a scanning electron microscopic study," Journal of Dental Sciences 5(1):14-20.

Hilton, 2009, "Keys to Clinical Success with Pulp Capping: A Review of the Literature," Operative Dentistry 34(5):615-625.

Kiatwateeratana et al., 2009, "Partial pulpotomy on caries-free teeth using enamel matrix derivative or calcium hydroxide: a randomized controlled trial," International Endodontic Journal 42(1):584-592.

Kim et al., 2021, "Comparison and Contrast of Bone and Dentin in Genetic Disorder, Morphology and Regeneration: A Review," Journal of Bone Metabolism 28(1):1-10.

Pellegrini et al., 2016, "Human pulps capped with PDGF: A pilot study," Journal of Oral Science and Rehabilitation 2(3):34-41.

PULP CAPPING METHODS

CROSS-REFERENCE TO RELATED APPLICATIONS

This application is a continuation of U.S. patent application Ser. No. 17/363,827, filed Jun. 30, 2021, the disclosure of which is incorporated by reference herein its entirety.

TECHNICAL FIELD

Disclosed herein are methods of pulp capping exposed pulp in a tooth for pulpal revitalization and/or inducing dentin formation or regeneration.

BACKGROUND

Teeth are composed of dental tissues, which include enamel, dentin, cementum and pulp. FIG. 1 shows a mammalian tooth 10 with a protective outer layer of enamel 20. Pulp 30 in the central portion of the tooth 10 is filled with blood vessels and nerves, which enter through the root canals into the pulp chamber 32, where there is the pulp chamber floor 33 and the pulp chamber roof, which typically has sites where the pulp extends the base of dentinal structure, which individually are each termed a pulp horn 31. Surrounding the pulp 30 is dentin 40.

Pulp capping is a dental procedure used to cover pulp of a tooth that has become exposed due to reasons such as tooth decay, trauma, or when removing decay from a tooth. Pulp capping on exposed pulp facilitates the formation of protective barrier and maintenance of the pulp (Komabayashi et al., 2016, *Dental Materials Journal* 35(1):1-12), If undertaken early, that is, before pulp necrosis, pulp capping may help to avoid root canal treatment or tooth extraction. Materials used in pulp capping to cover the exposed pulp have included zinc oxide eugenol, glass ionomer/resin-modified glass ionomer, calcium hydroxide ("$Ca(OH)_2$") and mineral trioxide aggregate ("MTA"). Certain pulp capping materials have been described, e.g., in U.S. 2008/0318190 A1.

Following pulp capping, a dentin-like structure may form between the pulp capping material and pulp, however with $Ca(OH)_2$ and MTA, however this dentin-like structure has been reported to be porous and/or form an incomplete layer (see, e.g., Al-Hezaimi et al., 2011, *J. Endod.,* 37:507-512). Applying biological molecules such as growth factors and extracellular matrices have been used when pulp capping to stimulate tissue regeneration and growth, including, for example, bone morphogenetic proteins (BMPs) and enamel matrix derivative (EMD), although results have been variable (see, e.g., Komabayashi et al., 2016, *Dental Materials Journal* 35(1):1-12). EMDOGAIN® gel (Straumann) is a commercial EMD product containing amelogenins, a type of extracellular matrix protein, which has successfully been employed to restore cementum and alveolar bone. Randomized controlled clinical trials on the use of EMD with permanent filling (without pulp capping material) for direct pulp capping in primary molars and partial pulpotomy in permanent premolars failed to observe dentin regeneration (Garrocho-Rangel et al., 2009, *Oral Surg. Oral Med. Oral Pathol. Oral Radiol. Endod.,* 107:733-738; Kiatwateeratana et al., 2009, *Int. Endod. J.,* 42:584-592).

Platelet-derived growth factor ("PDGF") is potent mitogen for a variety of cell types. PDGF is a protein dimer which can include two A subunits ("PDGF-AA"), two B subunits ("PDGF-BB") or one of each ("PDGF-AB"). It has been reported that PDGF-BB plays a role in periodontal bone and dental tissue regeneration when used in conjunction with bone allograft and PDGF-BB gene modified human dental pulp stem cells, respectively (Nevins et al., 2003, *Periodontal.,* 74:1282-1292; Zhang et al., 2017, *Stem* Cells Transl. Med., 6:2126-2134). When recombinant human PDGF was used without a matrix on human dental pulp stem cells insignificant dentinal tissue formation was reported (Zhang et al., 2008, *Tissue Eng. Part A,* 14:285-294; Zhang et al., 2006, *Biomaterials,* 27:5658-5668).

BRIEF SUMMARY

Disclosed herein are methods, e.g., of pulp capping and pulp revitalization of an exposed pulp in a tooth comprising administering a growth factor substance (e.g., platelet-derived growth factor (PDGF) or enamel matrix derivative (EMD)) to exposed pulp in a tooth, followed by placing a pulp capping material (e.g., mineral trioxide aggregate (MTA) or calcium hydroxide) over the exposed pulp.

In one aspect, disclosed herein are methods of pulp capping exposed pulp in a tooth comprising administering a growth factor substance (e.g., PDGF or EMD) to exposed pulp in a tooth, and placing a pulp capping material (e.g., MTA or calcium hydroxide) over the exposed pulp after administering the growth factor substance (e.g., PDGF or EMD).

In some embodiments, the method comprises:

(a) administering recombinant human platelet-derived growth factor (rhPDGF) or enamel matrix derivative (EMD) to exposed pulp in the tooth; and (b) placing mineral trioxide aggregate (MTA) or calcium hydroxide over the exposed pulp following step (a).

In certain embodiments, rhPDGF is administered in step (a).

In certain embodiments, the exposed pulp is in a cavity in the tooth, wherein the placed MTA or calcium hydroxide seals the cavity, and the method further comprises step (c) applying a permanent filling over the placed MTA or calcium hydroxide.

In certain embodiments, the exposed pulp is in a cavity in the tooth and the method further comprises step (c) sealing the cavity with a permanent dental filling following step (b).

In certain embodiments, the exposed pulp is in a cavity in the tooth and the method further comprises step (c) sealing the cavity containing the placed MTA or calcium hydroxide with a permanent dental filling.

In certain embodiments, the calcium hydroxide is placed in step (b).

In certain embodiments, repaired dentin forms between the site of the exposed pulp and the placed calcium hydroxide.

In certain embodiments, the MTA is placed in step (b).

In certain embodiments, regenerated dentin forms between the site of the exposed pulp and the placed MTA.

In certain embodiments, the MTA is placed to be in contact with dentin at the periphery of the site of exposed pulp.

In certain embodiments, the rhPDGF is rhPDGF-BB.

In certain embodiments, the MTA is placed over the site of exposed pulp at least 1 minute, at least 2 minutes, at least 3 minutes, at least 4 minutes, at least 5 minutes, or at least 10 minutes after administering step (a).

Also provided herein are methods of inducing dentin formation over exposed pulp in a cavity of a tooth. In certain embodiments, the method of inducing dentin formation comprises administering a growth factor substance (e.g., PDGF or EMD) to exposed pulp in the tooth, and placing a pulp capping material (e.g., MTA or calcium hydroxide) over the exposed pulp.

In certain embodiments, the method of inducing dentin formation comprises administering a growth factor substance (e.g., PDGF or EMD) to exposed pulp in the tooth, followed by placing a pulp capping material (e.g., MTA or calcium hydroxide) over the exposed pulp.

In some embodiments, a method of inducing dentin formation produces regenerated dentin.

In certain embodiments, provided herein is a method of inducing dentin regeneration over exposed pulp in an access cavity of a tooth, the method comprising:

(a) administering rhPDGF) to the exposed pulp;
(b) placing MTA over the exposed pulp after step (a), wherein the placed MTA is in contact with dentin at a periphery of the exposed pulp; and
(c) sealing the access cavity with a permanent dental filling after step (b); whereby regenerated dentin is formed in the tooth between the pulp and the placed MTA.

DETAILED DESCRIPTION

Figure 1:
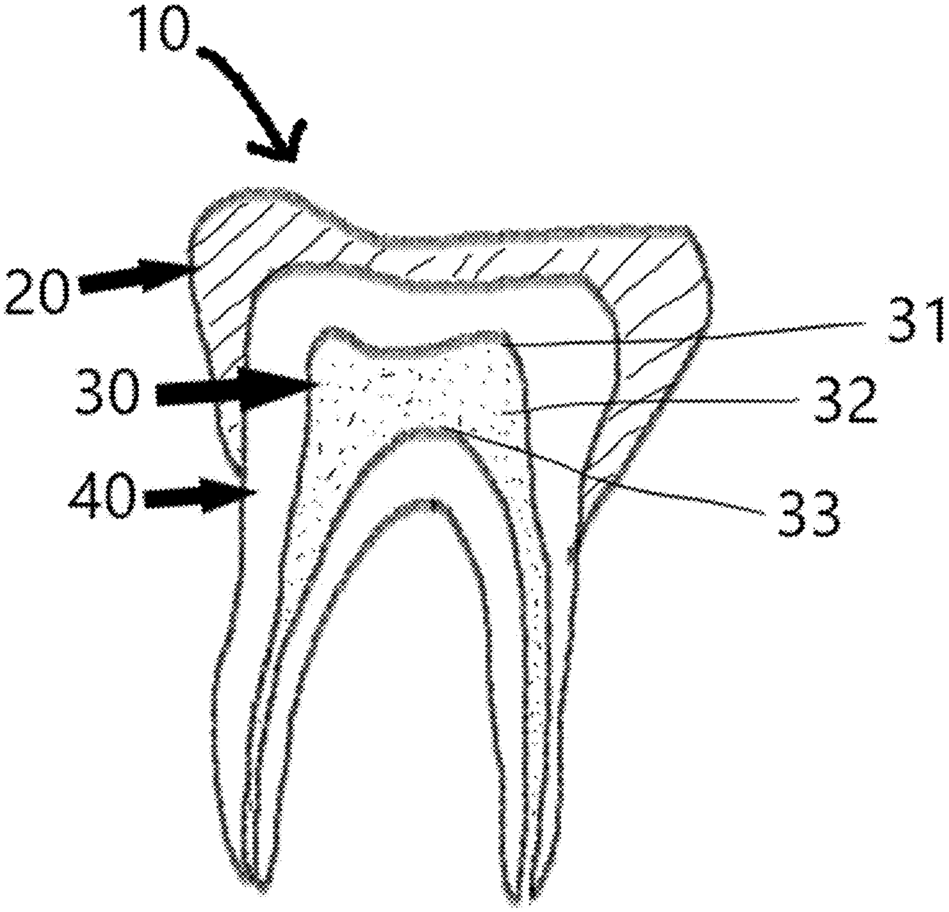
FIG. 1 depicts a cross-section rendering of a tooth indicating its tissue layers.

Provided herein are methods of pulp capping using a combination of compositions that are demonstrated herein to facilitate growth of new dentin or dentin-like tissue over exposed pulp in a tooth. Dentin formation over exposed pulp is advantageous, e.g., for preserving pulp vitality, preventing complete pulp infection, protecting the pulp from noxious agents, and the like.

In general, methods provided herein comprise administering a growth factor substance, which can, for example, be platelet-derived growth factor (PDGF) or enamel matrix derivative (EMD), to exposed pulp, followed by placing a pulp capping material, which can, for example, be mineral trioxide aggregate (MTA) or calcium hydroxide, over the exposed pulp.

In one aspect, provided herein are methods of pulp capping exposed pulp in a tooth.

In some embodiments, a method of pulp capping exposed pulp in a tooth comprises (a) administering platelet-derived growth factor (PDGF) or enamel matrix derivative (EMD) to exposed pulp in the tooth; and (b) placing mineral trioxide aggregate (MTA) or calcium hydroxide over the exposed pulp following the administration step (a).

In another aspect, methods of inducing dentin regeneration over exposed pulp in a cavity of a tooth are provided herein.

In another aspect, methods are provided for revitalizing pulp tissue in a tooth with exposed and/or inflamed pulp.

In certain embodiments of a method for inducing dentin regeneration over exposed pulp in a tooth, the method comprises: (a) administering EMD or PDGF to the exposed pulp in a cavity of the tooth; (b) placing MTA or calcium hydroxide over the exposed pulp after step (a), wherein the MTA or the calcium hydroxide is in contact with dentin at a periphery of the exposed pulp; (c) sealing the cavity with a permanent dental filling after step (b); whereby dentin is regenerated between the pulp and the MTA or the calcium hydroxide.

In certain embodiments of a method for inducing dentin regeneration over exposed pulp in a tooth, the method comprises: (a) administering PDGF to the exposed pulp in a cavity of the tooth; (b) placing MTA over the exposed pulp after step (a), wherein the MTA is in contact with dentin at a periphery of the exposed pulp; (c) sealing the cavity with a permanent dental filling after step (b); whereby dentin is regenerated between the pulp and the MTA.

Those skilled in the art will know that direct pulp capping is used when the pulp is visibly exposed, which can be due to, for example, caries, trauma, or accidental exposure during tooth preparation or caries removal. Indirect pulp capping is generally used in deep cavity preparation that may be in close proximity to the pulp but with no visible pulp exposure.

Unless referred to as "indirect pulp capping," the term "pulp capping" as used herein refers "direct pulp capping."

The terms "subject" and "patient" are used herein interchangeably, and will generally be understood to mean a human subject unless denoted otherwise. It will be understood that the methods provided herein are performed on a tooth in a subject. In certain embodiments of the methods provided herein, the subject can be a mammal, such as, e.g., chimpanzee, baboon, gorilla, horse, goat, dog, or pig.

The term "dentin formation," as used herein, refers to newly formed dentin or to newly formed dentin-like structure formed after pulp capping according to the methods provided herein.

The phrases "revitalizing pulp tissue" or "revitalized pulp tissue" as used herein means that a tooth with exposed pulp that exhibits thermal (hot or cold) sensitivity, pain, and/or other indications indicative of pulpitis, returns to a state where the tooth does not exhibit thermal (hot or cold), pain, and/or other indications of pulpitis after pulp capping as described herein.

It is generally understood in the art that dentin can be classified as primary dentin, which is formed only early in tooth development. Secondary dentin, which formed after root formation is complete, and continues to grow, albeit slowly, in the mature tooth. Secondary dentin is similar to primary dentin although there are noticeable morphological differences between primary and secondary dentin. Tertiary dentin, which includes so-called reactionary dentin, is distinct in structure from primary and secondary dentin, and typically grows only in reaction to external stimuli.

As used herein, the term "regenerated dentin" means newly formed dentin that resembles secondary dentin in its morphology or structure when subject to histological analysis.

As used herein, the term "repaired dentin" means a dentin-like structure that does not resemble secondary dentin in its morphology or structure when subject to histological analysis.

Prior to pulp capping, clinical pulp conditions can be evaluated, which can be performed using diagnostic tests known in the art. Pulp capping typically would not be performed on a tooth were pulp necrosis is diagnosed. While normal pulp has no clinical symptoms, pulp with reversible pulpitis usually has a short-lived thermal sensitivity, which will disappear immediately once the thermal stimulation is removed. Irreversible pulpitis can, for example, have spontaneous, and/or lingering pain.

In certain embodiments of the methods provided herein, the method is performed on a tooth wherein the pulp is normal pulp, or the pulp has reversible pulpitis.

In certain embodiments, the method is performed on a tooth wherein the pulp has irreversible pulpitis.

Typically, pulp capping can be performed where percussion, palpation, and thermal test results confirm vital pulp diagnosis. Radiography should show normal apical tissue.

Techniques for drilling to create a cavity in the tooth are well known in the art, for instance, to allow access to administer growth factor substance (e.g., PDGF or EMD), and placing pulp capping material (e.g., MTA or calcium hydroxide). For instance, the clinician can employ high speed or low speed drills to create an access cavity and/or, for instance, to remove any decayed or infected tissue.

The term "access cavity" as used herein refers to a space created in the tooth containing exposed pulp in which the growth factor substance (e.g., PDGF or EMD) can be administered and/or in which the pulp capping material (e.g., MTA or calcium hydroxide) can be placed.

In certain embodiments, the pulp exposure site is visible and less than 1 mm in diameter. In some embodiments the pulp exposure site is visible and less than 1.5 mm in diameter, less than 2 mm in diameter, less than 2.5 mm in diameter, or is less than 3.0 mm in diameter.

Prior to administering any material over the exposed pulp, any pulpal hemorrhage should be stopped. For instance, bleeding can be stopped by placing a cotton pellet soaked in a solution on the exposed pulp. Solutions that can be administer to the exposed pulp to control bleeding can, for instance, be saline, sodium hypochlorite, hydrogen peroxide, ferric sulfate, and chlorhexidine. Typically, sodium hypochlorite is administered.

In certain embodiments of the methods provided herein, the methods comprise administering PDGF to the exposed pulp in the tooth and placing MTA or calcium hydroxide over the exposed pulp following the administration of the PDGF. In some embodiments, MTA is placed over the exposed pulp following the administration of the PDGF. In yet other embodiments, calcium hydroxide is placed over the exposed pulp following the administration of the PDGF.

In some embodiments the PDGF is PDGF-AA, PDGF-BB, or PDGF-AB. For instance, the PDGF can be human recombinant PDGF ("rhPDGF"). In certain embodiments, the PDGF is rhPDGF-BB. rhPDGF-BB is well known in the art and is commercially available, for example, from Akron Biotech (Boa Raton, FLA). Commercial sources of rhPDGF-BB suitable for use in the methods described herein also include the GEM21S® growth factor enhanced matrix product (Lynch Biologics LLC).

In certain embodiments, the PDGF is administered in a liquid formulation. In some embodiments, the PDGF is administered in a gel formulation.

PDGF can, for instance, be applied directly to the site of exposed pulp. Administration can be using a syringe, or other applicator suitable for delivering the PDGF to contact the exposed pulp. The amount of PDGF administered can, for example, be between 1.0 μg to 1.0 mg. In certain embodiments the amount of PDGF administered is between 5.0 μg to 300 μg, between 10 μg to 100 μg, between 15 μg to 50 μg, or between 15 μg to 30 μg. For example, a drop (or a volume in the range of 10 μL to 200 μL, more typically between 50 μL to 100 μL) of rhPDGF-BB in solution is administered by being deposited on the exposed pulp, where the concentration of rhPDGF-BB can be between 0.1 mg/mL to 1.0 mg/mL, or 0.2 mg/mL, 0.3 mg/mL, 0.5 mg/mL in the solution.

In some embodiments provided herein is a method of pulp capping exposed pulp in a tooth comprising (a) administering rhPDGF-BB or EMD to exposed pulp in the tooth; and (b) placing MTA over the exposed pulp following step (a).

In some embodiments provided herein is a method of pulp capping exposed pulp in a tooth comprising (a) administering rhPDGF-BB to exposed pulp in the tooth; and (b) placing MTA or calcium hydroxide over the exposed pulp following step (a).

In some embodiments provided herein is a method for inducing dentin regeneration over exposed pulp in a cavity of a tooth, comprising (a) administering EMD or rhPDGF=BB to the exposed pulp in the cavity of the tooth; (b) placing MTA over the exposed pulp after step (a); whereby dentin is regenerated between the pulp and the MTA.

In some embodiments provided herein is a method for inducing dentin regeneration over exposed pulp in a cavity of a tooth, comprising (a) administering rhPDGF=BB to the exposed pulp in the cavity of the tooth; (b) placing MTA or calcium hydroxide over the exposed pulp after step (a); whereby dentin is regenerated between the pulp and the MTA.

In certain embodiments of the methods provided herein, the methods comprise administering EMD to the exposed pulp in the tooth, and placing MTA or calcium hydroxide over the exposed pulp following the administration of the EMD. In some embodiments, MTA is placed over the exposed pulp following the administration of the EMD. In other embodiments, calcium hydroxide is placed over the exposed pulp following the administration of the EMD.

EMD is a sterile protein aggregate prepared from extracting proteins from porcine immature enamel matrix. EMD is one of the most widely used biologic agents used in periodontics. EMD is marketed, for example, as EMDOGAIN® (Straumann USA, LLC).

In certain embodiments, the EMD is administered in a liquid formulation. In some embodiments, the EMD is administered in a gel formulation.

EMD can, for instance, be applied directly to the site of exposed pulp. Administration can be using a syringe, or other applicator suitable for delivering the EMD to contact the exposed pulp. The amount of EMD administered can, for example, be between 0.05 mg to 10 mg. In certain embodiments the amount of EMD administered is between 0.1 mg to 5.0 mg, between 0.5 mg to 4.0 mg, between 1.0 mg to 3.5 mg, or between 1.5 mg to 3.0 mg.

In certain embodiments, EMD in a gel formulation comprising between 1 mg/mL to about 50 mg/mL, e.g., 10 mg/mL, 20 mg/mL, or 30 mg/mL protein, is administered in a volume between 10 μL to 200 μL, e.g., between 50 μL to 100 μL.

In some embodiments, a drop of EMDOGAIN® EMD directly from the syringe as provided by the manufacturer can be deposited on the exposed pulp to administer the EMD.

Once the growth factor substance (e.g., PDGF or EMD) is administered to the exposed pulp, a period of time can be allowed to pass prior to placing the pulp capping material (e.g., calcium hydroxide or MTA) over the exposed pulp. For instance, in certain embodiments, the pulp capping material is placed over the exposed pulp at least one minute after administering the growth factor substance. In some embodiments, the pulp capping material is placed over the exposed pulp at least 2 minutes, at least 3 minutes, at least 4 minutes, at least 5 minutes, or at least 10 minutes after administering the growth factor substance. In certain embodiments, the pulp capping material is placed over the exposed pulp at least 15 minutes, at least 30 minutes or at least 1 hour after administering the growth factor substance. In some embodiments, the pulp capping material is placed over the exposed pulp between 1 to 10 minutes after administering the growth factor substance.

Following the administration of the growth factor substance (e.g., PDGF or EMD), a pulp capping material (e.g., calcium hydroxide or MTA) is placed over the exposed pulp. In certain embodiments, the pulp capping material is calcium hydroxide. In some embodiments, the pulp capping material is MTA.

Pulp capping materials are well known in the art, including calcium hydroxide and MTA. As will be known to those skilled in the art, suitable calcium hydroxide and MTA for use in the methods described are readily available from a number of manufacturers.

The pulp capping material (e.g., calcium hydroxide or MTA) can, for example, be placed over the exposed pulp according to any technique known to those skilled in the art. When placing the pulp capping material (e.g., calcium hydroxide or MTA) in the cavity, for instance, care should be taken to prevent trauma to the remaining pulpal tissue and to ensure continuous coronal seal of the root canal orifice and the access cavity.

In certain embodiments, the pulp capping material (e.g., calcium hydroxide or MTA) is placed to form a seal over the exposed pulp.

In certain embodiments of the methods provided herein, the pulp capping material (e.g., calcium hydroxide or MTA) is placed in contact with the exposed pulp.

In some embodiments, the pulp capping material (e.g., calcium hydroxide or MTA) is placed to be in contact with dentin at the periphery of the site of the root canal orifice.

In some embodiments, the pulp capping material (e.g., calcium hydroxide or MTA) is placed to be in contact with dentin at the periphery of the site of exposed pulp.

In some embodiments, the pulp capping material (e.g., calcium hydroxide or MTA) is placed such that any exposed pulp is covered by the pulp capping material (e.g., calcium hydroxide or MTA).

In some embodiments, the pulp capping material (e.g., calcium hydroxide or MTA) is placed such that any exposed dentin is covered by the pulp capping material (e.g., calcium hydroxide or MTA).

In certain embodiments of the methods provided herein, the method further comprises sealing the access cavity containing the placed pulp capping material (e.g., calcium hydroxide or MTA) with a permanent dental filling.

Typically the permanent dental filling will be applied over the pulp capping material (e.g., calcium hydroxide or MTA). The permanent dental filling can, for instance, form a seal with the dentin and/or enamel to completely close off the access cavity in which the pulp capping material (e.g., calcium hydroxide or MTA) was placed.

Suitable permanent dental fillings for use in the methods provided herein are well known in the art. For instance, the permanent dental filling can be an amalgam filling, a composite filling (or filled resin filling), gold filling, silver filling, ceramic filling, or a glass ionomer filling.

Figure 15:
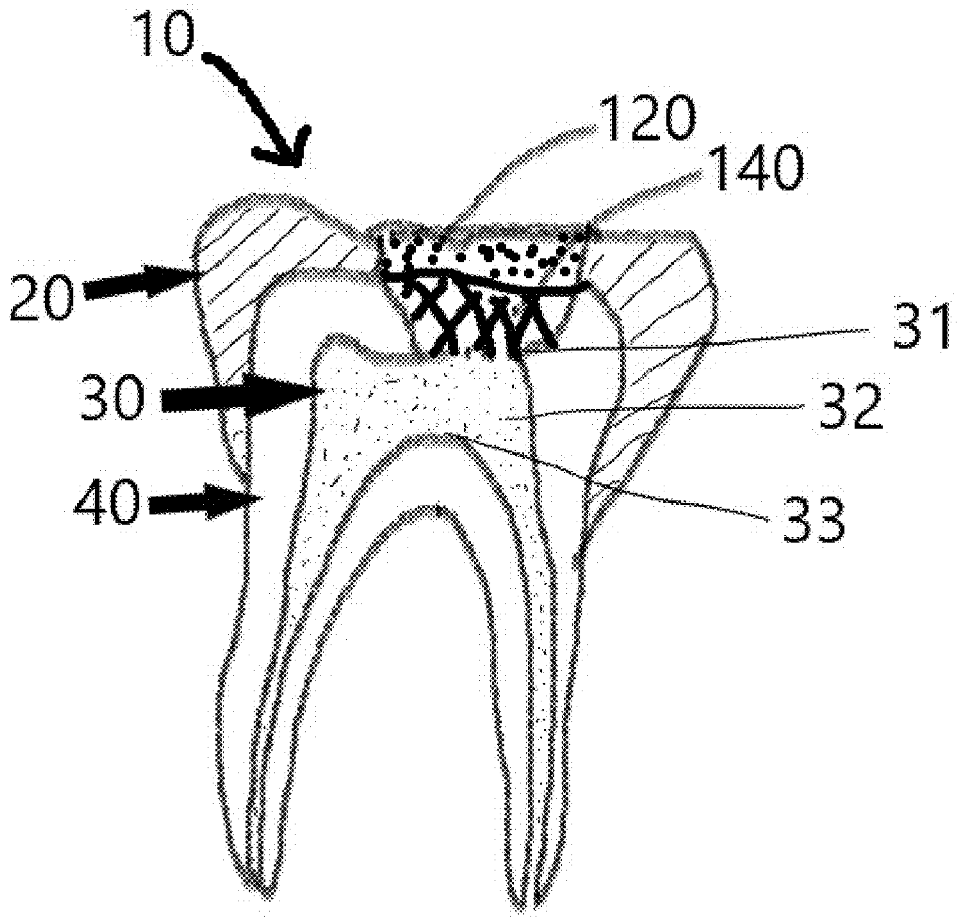
FIG. 15 depicts a cross-section rendering of a tooth after pulp capping.

FIG. 15 shows a rendering of exemplary pulp-capped tooth in which a cavity in the tooth where the pulpal horn 31 was exposed in the cavity making a site of exposed pulp 30. The cavity is filled with pulp capping material 140 placed into the cavity in contact with dentin 40. Permanent dental filling 120 is overlaid on the pulp capping material 140 to seal the cavity.

In certain embodiments, a method as described herein is performed on a permanent tooth.

In some embodiments, the tooth is a primary (baby) tooth.

According to the methods provided herein, regenerated or repaired dentin can be newly formed between the site of exposed pulp and pulp capping material (e.g., calcium hydroxide or MTA).

In certain embodiments, the newly formed dentin is regenerated dentin.

In some embodiments, the newly formed dentin is repaired dentin.

In some embodiments, the newly formed dentin is regenerated secondary dentin.

In some embodiments, the newly formed dentin is restored secondary dentin.

In yet other embodiments provided herein are methods for pulp capping a tooth or for inducing dentin formation over exposed pulp in a cavity of a tooth, comprising (a) administering rhPDGF and EMD to exposed pulp in a cavity of the tooth; and (b) placing MTA or calcium hydroxide over the exposed pulp after step (a).

It will be understood that the growth of newly formed dentin is a process that takes time after the pulp capping procedure. In certain embodiments of the methods provided herein, regenerated dentin or restored dentin can be newly formed after 3 weeks, after 4 weeks, after 5 weeks, after 6 weeks, after 7 weeks, after 2 months, after 3 months, after 4 months, or after 5 month following pulp-capping.

In certain embodiments of the methods provided herein, dentin formation occurs between the site of exposed pulp and the pulp capping material (e.g., calcium hydroxide or MTA).

In certain embodiments, the method for revitalizing pulp tissue in a tooth with exposed pulp comprises administering PDGF or EMD to the exposed pulp followed by placing MTA or calcium hydroxide over the exposed pulp.

In some embodiments, PDGF is administered followed by placing MTA or calcium hydroxide over the exposed pulp.

In some embodiments, the method further comprises adding a permanent dental filling to the tooth after placing the MTA or calcium hydroxide.

EXAMPLES

Example 1

This example describe results of the effect of $Ca(OH)_2$, termed CaOH2 herein, as a matrix carrier for rhPDGF and EMD on inducing dentin formation following pulp capping. In the study described in this example, pulp capping was performed on premolar teeth in human subjects, and the teeth extracted 4 months after pulp capping for histomorphometric and micro-computed tomography (micro-CT) analyses.

Material and Methods

Sources for materials were as follows: $Ca(OH)_2$, DYCAL calcium hydroxide composition (Dentsply Sirona); EMD, EMDOGAIN® gel (Straumann), rhPDGF, GEM21 (Osteohealth). A randomized clinical trial protocol was followed, which had been approved by the King Saud University Institutional Research Review Board and the in vivo Ethical Committee. Subjects enrolled in the study signed a consent form. Intact premolars scheduled for extraction due to orthodontic reasons were included in this trial. All teeth were tested for symptoms and pulp responses and proved normal. Class I occlusal caries were seen in 17 teeth, and 1 tooth had Class II occlusomesial caries. Eighteen premolars (from eight patients) were randomly assigned, using a brown bag, to one of three experimental groups: Group 1 (CaOH2 only); Group 2 (CaOH2+EMD); or Group 3 (CaOH2+rhPDGF). All patients received phone calls the night of the procedure and at 24 hours, 48 hours, and 1 week postoperatively to record any complaint of symptoms. None of the subjects reported lingering pain or swelling, and no patient was excluded from the study. No patient was excluded from the study or required root canal treatment at any stage of the experiment.

Pulp Exposure. Local infiltration with anesthetic solution of Xylocaine (20 mg/mL; Fresenius) and epinephrine (12.5 mg/mL) was used. Following application of a dental dam, the pulp of each tooth was exposed by creating a 4-mm—diameter occlusal Class I access cavity using a size 2 round bur mounted on a highspeed handpiece. Sterile saline solution was used as coolant. Bleeding was controlled with sterile cotton pellets followed by 2.5% sodium hypochlorite (NaOCl) irrigation. Each tooth was then left exposed to the oral cavity for 1 hour to obtain a nonsterile wound. Subsequently, the exposed pulp was irrigated with 2.5% NaOCl. After arrested bleeding was confirmed, the pulp was capped with one of the three experimental biomaterials. In Groups 2 and 3, a small drop of EMD (30 mg/mL) or GEM21 (0.3 mg/mL), respectively, was placed over the exposure site and left undisturbed for at least 1 minute. CaOH2 was then mixed and carefully placed with gentle pressure over the control site (group 1) or over the EMD or GEM21 (Groups 2 and 3, respectively) and the adjacent dentin in the exposure site to ensure close contact with the pulp tissue. Amalgam filling was then placed over the pulp-capping material to seal the coronal access cavity.

Periapical radiographs were taken preoperatively, immediately following the procedure, and 4 months later. Under local anesthesia, teeth were atraumatically extracted 4 months after the pulp capping procedure. Clinical tests, including percussion, palpation, electric pulp test, and thermal tests, were done in all teeth prior to extraction. All teeth responded normally.

Micro-Computed Tomography (micro-CT) Analysis. The extracted teeth were fixated in 10% phosphate-buffered formaldehyde (pH 7.4) and dehydrated in 70% ethanol. Using a scanner (model 1172; SKY SCAN, Bruker), Micro-computed tomography was performed to assess the density, thickness, and continuity of the newly formed hard tissue, as well as the presence of calcifications in the root canal space. Each tooth was wrapped in PARAFILM (Pechiney Plastic Packaging) to prevent desiccation during scanning. Specimens were scanned at 100 kV and 100 mA with a resolution of 18.6 mm, using a 0.5-mm—thick aluminum filter and 54% beam-hardening reduction. After image reconstruction, two-dimensional virtual slices were acquired in the axial plane and examined corono-apically and mesiodistally to determine the first and last slices in which reparative hard tissues could be identified. This provided a rough estimate of the thickness of the newly formed hard tissues. Every tenth slice (0.186 mm apart) was used to create a serial profile of the newly formed hard tissues.

Light Microscopy. The teeth were decalcified for 10 weeks using a solution containing equal parts of 50% formic acid and 20% sodium citrate. Following decalcification, the specimens were washed in running water, dehydrated in ascending ethanol series, and embedded in paraffin. Polymerized blocks were primarily grounded to bring the tissue components closer to the cutting surface. A 100-μm—thick section attached to the second slide was cut under 50- to 100-g pressure using diamond blade saw. A final thickness of 40 μm was achieved by grinding and polishing each specimen with 1,200-, 2,400-, and 4,000-grit sandpaper. The sections were then stained with toluidine blue/pyronin.

Histologic analysis was performed using an image analysis system (OMNIMET 9.5, Buehler) linked to a light microscope. Pixel calibration was performed by using a digitized image of a Stage Micrometer for Transmitted Light (Ted Pella, Inc.). Magnifications were between ×2 and ×32.

Data Analysis. Histomorphometric and micro-CT analyses were used to assess the presence and pattern of the newly formed hard tissue structure, continuity (mesiodistally and buccolingually), form, thickness, mineralization pattern, density, and organization. The histologic images were correlated with the corresponding micro-CT images. Outcomes from both histologic and micro-CT examinations were classified as either dentin regeneration or dentin repair. Regeneration was defined as restoration of the lost dentin that resembled secondary dentin in form and shape. Repair was defined as newly formed dentin-like structure that did not resemble secondary dentin in form and shape. Data sets were statistically analyzed using Kruskal-Wallis analysis of variance and Dunn multiple comparison tests to determine whether differences in the thickness of the reparative hard tissues existed among the three experimental groups. Statistical significance was predetermined at a 95% level of confidence. Thicknesses reported below are an average from teeth within a group.

Results

Group 1: CaOH2

Figure 2:
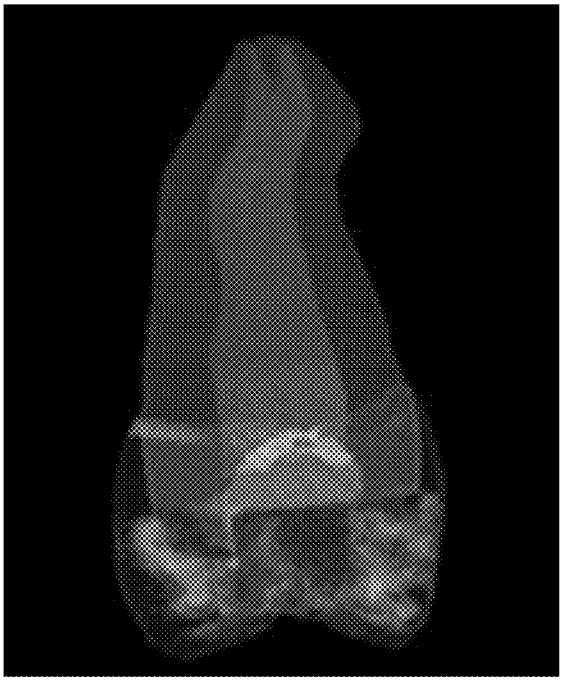
FIG. 2 depicts a micro-CT color-contrasted image from a tooth 4 months after pulp capping with $Ca(OH)_2$ alone. This image shows defective newly formed dentin-like structure (blue=amalgam; red=$Ca(OH)_2$; orange=newly formed dentin).
Figure 3:
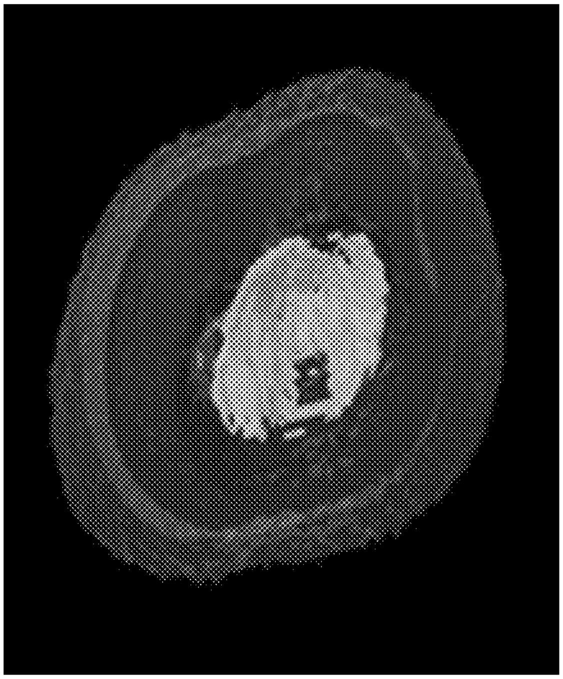
FIG. 3 depicts an occlusal micro-CT view of the same tooth as in FIG. 1 demonstrating that the newly formed dentin-like structure lacks the complete continuity in the buccolingual aspect to seal the pulpal tissue.
Figure 4:
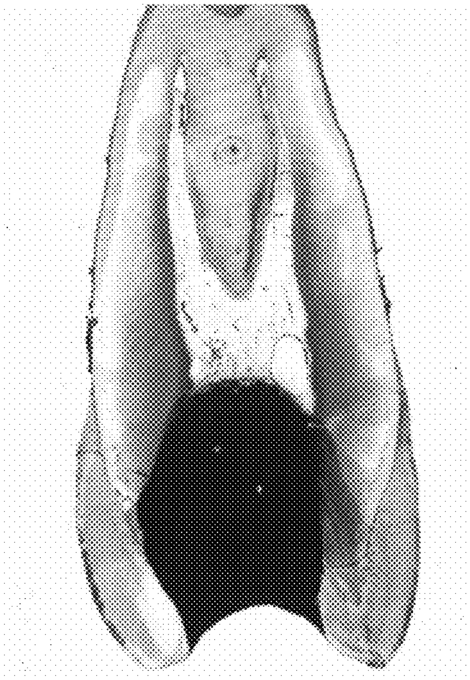
FIG. 4 depicts an image of a light microscopy section (×4 magnification) showing a complete tooth with a thin, newly formed dentin-like structure underneath the amalgam with no sign of root canal calcification from a tooth 4 months after pulp capping with $Ca(OH)_2$ alone.
Figure 5:
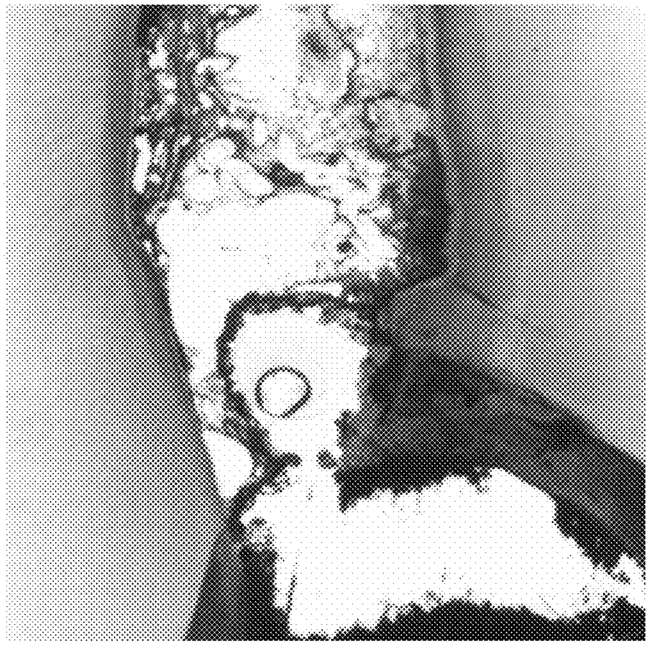
FIG. 5 depicts an image of the tooth of FIG. 4 taken under greater magnification (×32), showing the unorganized, thin, porous, and uneven thickness of the dentin-like structure.

Evidence of hard tissue apposition was minimal. Reconstructed three-dimensional (3D) micro-CT images showed a lack of continuity of newly formed dentin-like structure, resulting in direct communication between the pulp and the permanent filling material (FIG. 2 and FIG. 3). A very thin and highly porous layer of the newly formed structure was seen beneath the amalgam (FIG. 4 and FIG. 5). The pulp appeared normal with minimal inflammatory cells. The newly formed structure exhibited radiolucent tunnel defects and did not resemble secondary dentin in form, thickness, organization, or structure. Thickness of the newly formed structure was 0.18±0.084 mm measured histologically and 0.19±0.091 mm measured by micro-CT.

Group 2: CaOH2+EMD

Figure 6:
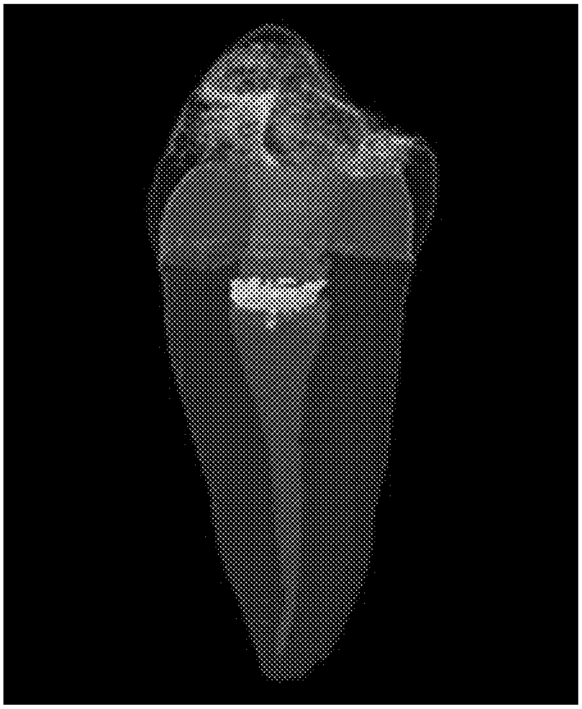
FIG. 6 depicts a reconstructed sagittal 3D micro-CT image showing the complete color contrasted tooth extracted 4 months after pulp capping with $Ca(OH)_2$+EMD (blue=amalgam; red=$Ca(OH)_2$; orange=newly formed dentin-like structure).
Figure 7:
FIG. 7 depicts a reconstructed sagittal 3D micro-CT image of tooth from FIG. 6 in a lateral sagittal view showing the newly formed dentin-like structure in complete continuity with secondary dentin in the tooth to form a seal over the pulp, where the newly formed dentin-like structure (orange) seals the pulpal orifice (where the root canal widens into the pulp chamber) with a high-density structure without presence of a significant porosity or apical root calcification.
Figure 8:
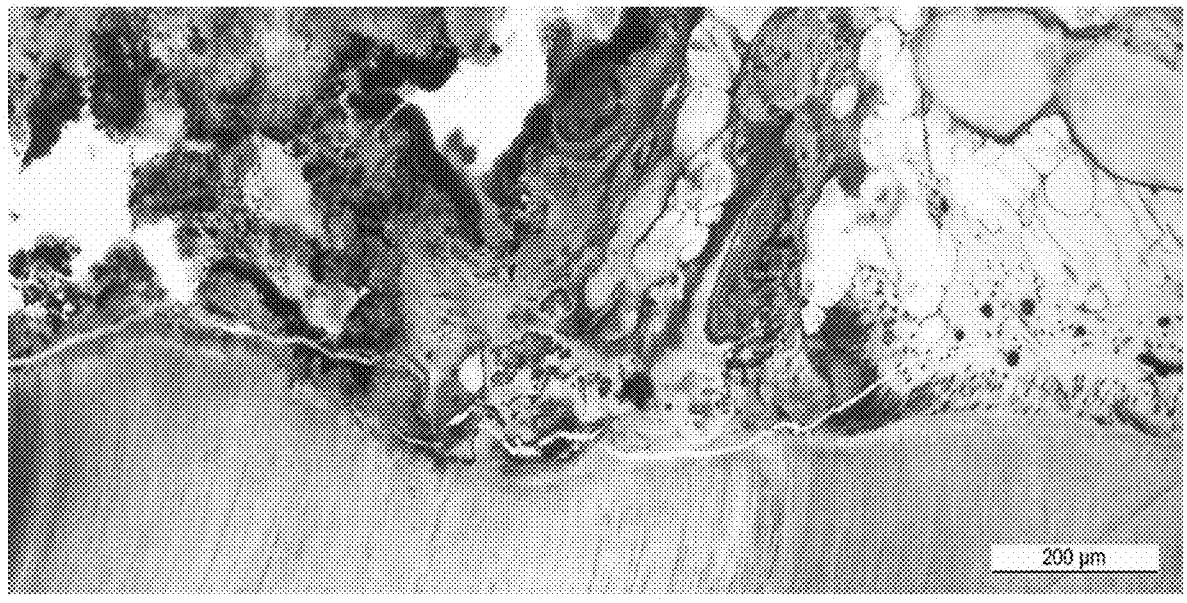
FIG. 8 depicts an image of a light microscopy section (×32 magnification) of a tooth extracted 4 months after pulp capping with $Ca(OH)_2$+EMD showing that the newly formed dentin-like structure is highly dense, nonporous, and without tunnel defects. It is associated with abundant odontoblast lacunae.

In one patient, the periapical radiograph at the 4-month follow up and reconstructed 3D micro-CT image showed evidence of a thick and uniform newly formed dentin-like structure. Histologic analysis and corresponding micro-CT images showed that a thick and continuous dentin-like structure formed beneath the amalgam and over the pulp tissue. Root canal obliterations in the apical root canal space were observed. The newly formed structure was characterized by a highly dense, nonporous appearance without tunnel defects seen in any cross-section slice examined by 3D micro-CT (FIG. 6 and FIG. 7). Abundant odontoblastic lacunae were associated with the newly formed structure and extensive areas of canal obliterations were observed (FIG. 8). In all specimens of this group, the pulp tissue was normal; the newly formed structure was atubular, nonporous, and highly dense; and it did not resemble secondary dentin. Thickness of the newly formed structure was 0.9±0.223 mm measured histologically and 0.94±0.178 mm measured by micro-CT (Table 1).

Of the various groups described in Examples 1 and 2, this group (CaHO2+EMD) was the only group to show root canal calcification (narrowing of the root canal).

TABLE 1

Histomorphometric and Micro-CT Analyses of Dentin Thickness and Histologic Findings

| | Analysis | | |
|---|---|---|---|
| | Histomorphometric | Micro-CT Analysis | Histologic Findings |
| Group 1: CaOH2 | 0.18 ± 0.084 mm | 0.19 ± 0.091 mm | Tunnel defects, incomplete dentin bridge, direct contact between pulp capping material and pulpal tissues associated with inflamed pulp. |
| Group 2: CaOH2 + EMD | 0.9 ± 0.223 mm | 0.94 ± 0.178 mm | Complete tissues bridge over pulpal space. Tissues do not represent secondary dentin. Highly dense tissue and absence of porosity. Root canal obliterations at the coronal and apical thirds were most frequent. |
| Group 3: CaOH2 + rhPDGF | 1.05 ± 0.19 mm | 1.04 ± 0.20 mm | Complete dentinal bridge, sealing the pulpal space with consistent dentin tissues thickness. It varied from secondary dentin in its low density, higher porosity, and different degree of mineralization. The histomorphometric and micro-CT analyses examined the newly formed tissue thickness over the pulpal space. |

Group 3: CaOH2+rhPDGF

Figure 9:
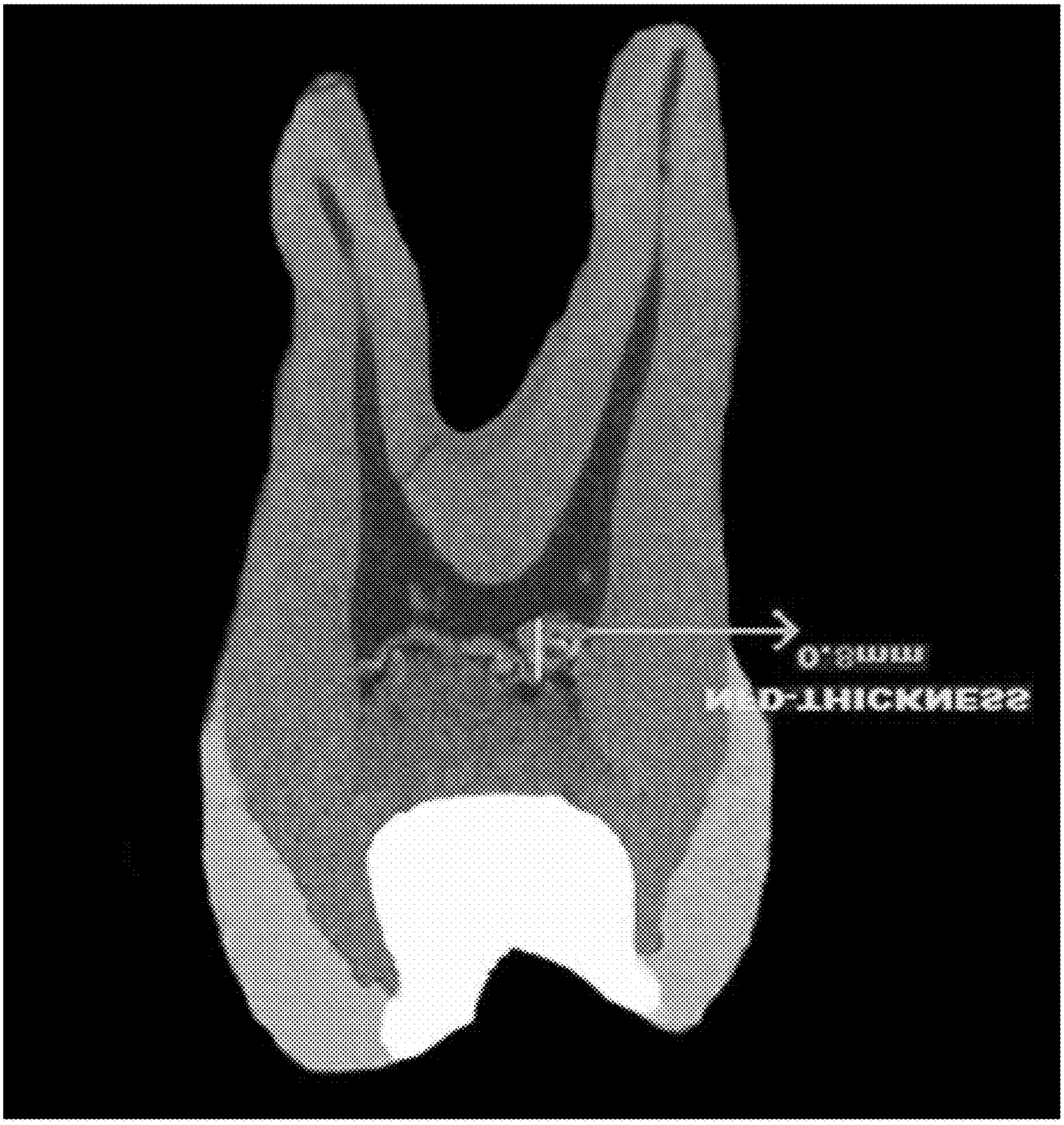
FIG. 9 depicts a reconstructed micro CT image showing a tooth extracted 4 months after pulp capping with $Ca(OH)_2$+rhPDGF, where the yellow line is drawn over 1.04±0.20-mm—thick newly formed dentin-like structure separating the $Ca(OH)_2$ and pulp tissue.
Figure 10:
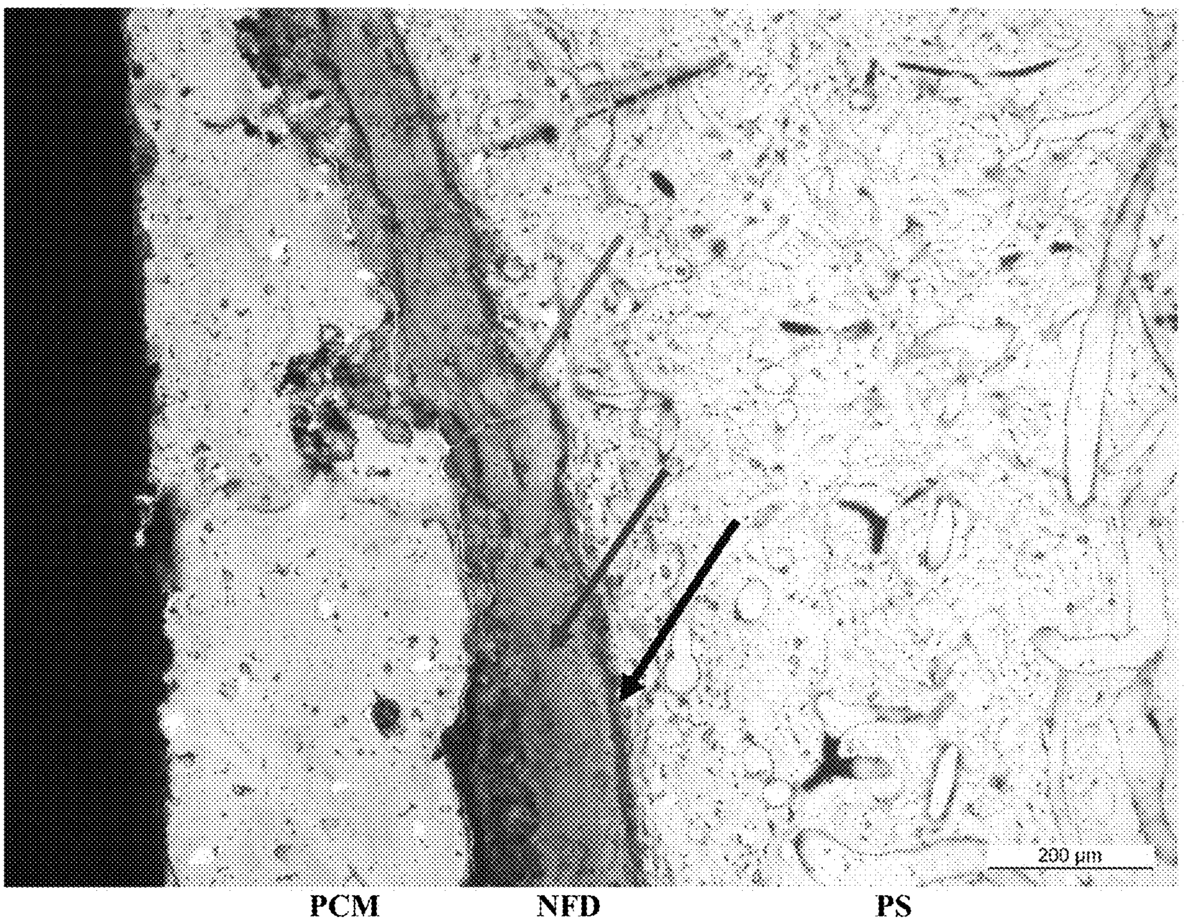
FIG. 10 depicts a histologic section taken under higher magnification (×32) of a tooth extracted 4 months after pulp capping with $Ca(OH)_2$+rhPDGF, showing a newly formed dentin-like structure with uneven thickness, as well as early (green arrow) and mature (red arrow) degrees of mineralization. Abundant odontoblast lacunae (black arrow) are present in all sides of the newly formed dentin-like structure. PCM=pulp capping material; NFD=newly formed dentin; PS=pulpal space.

Evidence of hard tissue formation was seen at the 4-month follow up. micro-CT images and corresponding histologic sections (e.g., FIG. 9) demonstrated significant thickness and complete 3D continuity of the newly formed dentin-like structure covering the pulp. No root canal obliterations were seen. Abundant odontoblast lacunae were present in all sides of the newly formed coronal and radicular structure. The thickness of the structure measured by reconstructed micro-CT analysis was similar to the histomorphometric measurement; however, the thickness was inconsistent. Different degrees of mineralization and high porosity of the newly formed structure were noted (e.g., FIG. 10) and were different in appearance from secondary dentin. The pulp tissue appeared normal with no sign of inflammation. Thickness of the newly formed structure was 1.05±0.19 mm measured histologically and 1.04±0.20 mm measured by micro-CT (Table 1).

The newly formed dentin-like structure in all groups was classified as repair. The difference in thickness of the newly formed structure between Groups 1 and 2 as compared to Group 3 were statistically significant ($P<0.05$). No significant differences in the thickness of the newly formed structure were found between Groups 2 and 3.

Discussion and Conclusion

Significant differences in newly formed dentin thickness were observed when CaOH2 was used alone as compared to CaOH2 used in combination with EMD or rhPDGF. The histologic, histomorphometric, and micro-CT analyses showed that all groups produced a dentin-like structure that was different from secondary dentin in form, density, shape, and thickness. Group 3 showed abundant odontoblastic lacunae, was without tunnel defects, had inconsistent hard tissue thickness, and had high porosity and low density. The different degrees of mineralization in the rhPDGF group could, for example, be due to the impact of CaOH2 hydroxylation, a production of carboxylate salts by chelation reaction combined with high alkalinity. This may affect the CaOH2 stability as a matrix for the rhPDGF during the early stage of wound healing. Recruitment of progenitor cells to sites of injury occurs naturally.

The mean thickness of the newly formed dentin-like structure was 0.18±0.084 mm, 0.9±0.223 mm, 1.05±0.19 mm for Groups 1, 2, and 3, respectively.

It is evident from the current findings that, when added to CaOH2, rhPDGF induced significant thickness in the newly formed dentin-like tissue, which differed from secondary dentin in its tissue density and mineralization.

The addition of CaOH2 to EMD resulted in significant root canal obliterations. The calcified tissue is unlike secondary dentin in form, shape, amount, and density. When rhPDGF is added to CaOH2, no calcific obliteration of root canals occurs. The newly calcified tissue differs from secondary dentin by degree of mineralization, porosity, and density. Adding rhPDGF to CaOH2 resulted in a tissue thickness over the pulp space that was more consistent, resembling secondary dentin. This example demonstrates the superior properties of pulp capping with CaOH2+PDGF over, e.g., CaOH2 used alone or CaOH2+EMD.

Example 2

This example describe results of the effect of mineral trioxide aggregate (MTA) as a matrix carrier for rhPDGF and EMD on dentin regeneration following pulp capping. In the study described in this example, pulp capping was performed on premolar teeth in human subjects, and the teeth extracted 4 months after pulp capping for histomorphometric and micro-computed tomography (micro-CT) analyses.

Material and Methods

Sources for materials were as follows: MTA (Dentsply Sirona); EMD, EMDOGAIN® gel (Straumann), rhPDGF, GEM21 (Lynch Biologics). The randomized clinical trial protocol used for the study described in this example was approved by the King Saud University Institutional Research Review Board and the in vivo Ethical Committee. Subjects enrolled in the study signed consent forms. Intact premolar human teeth scheduled for extraction due to orthodontic reasons were included. All teeth were tested for symptoms and pulp responses and proved normal. Eighteen premolars obtained from eight patients were randomly assigned, using a brown bag, to one of the following three experimental groups (n=6 teeth per group): Group 1, using MTA alone for pulp capping; Group 2, using MTA+EMD, or Group 3, using MTA+rhPDGF. All patients received phone calls the night of the procedure, and at 24 hours, 48 hours, and 1 week postoperatively to record any symptom complaints. None of the subjects reported lingering pain or swelling, and no patient was excluded from the study.

Pulp exposure was performed as described in the preceding example. After arrested bleeding was confirmed, the pulp was capped with one of the three experimental biomaterials. Group 1 was capped with MTA alone. In Group 2, a small drop of EMD (30 mg/ml) was placed over the exposure site and left undisturbed for at least 1 minute. In Group 3, a small drop of rhPDGF (50 microliters) was placed over the exposure site and left undisturbed for at least 1 minute. MTA was then mixed and carefully placed with gentle pressure over the EMD or rhPDGF as well as the adjacent dentin in the exposure site to ensure close contact with the pulp tissue. Amalgam filling was then placed over the pulp-capping material to seal the coronal access cavity.

Periapical radiographs were taken preoperatively and 4 months postoperatively. Four months following the pulp-capping procedure, the teeth were atraumatically extracted under local anesthesia. Clinical tests including percussion, palpation, electric pulp test, and thermal tests were done in all teeth prior to extraction. All teeth responded normally.

Extracted teeth were fixated, and micro-CT, light microscopy, histologic analysis and data analyses were performed as described in Example 1.

Results

Group 1: MTA

Figure 11A:
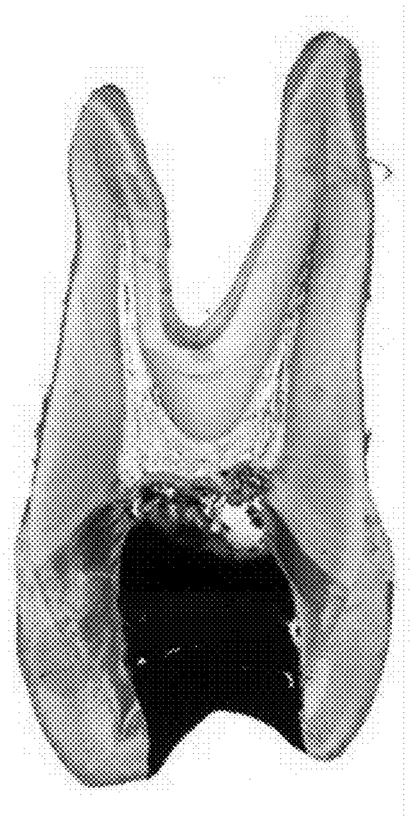
FIG. 11*a* and FIG. 11*b* depict histologic sections from light microscopy of a tooth extracted 4 months after being pulp capped with MTA under ×4 magnification and ×20 magnification, respectively. These show newly formed dentin-like structure that is not uniform in shape or form; however, it appears to have a consistent degree of mineralization and significant thickness.
Figure 11B:
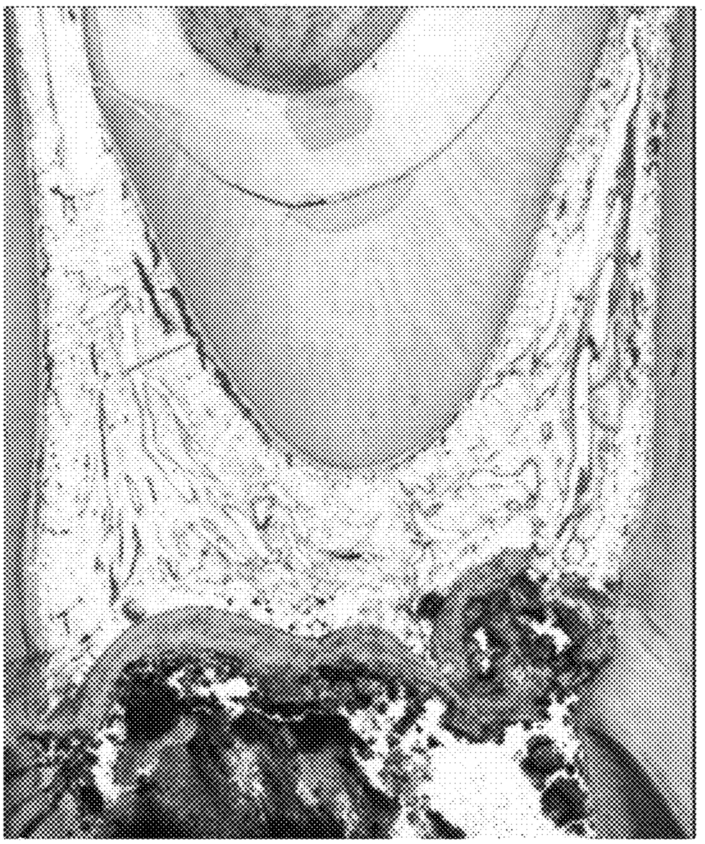

Minimal hard tissue formation was seen beneath the amalgam filling in the periapical radiograph, micro-CT images, and its corresponding histologic sections. The newly formed dentin-like structure had uneven thickness, and the pulp tissue exhibited inflammatory infiltrate (FIGS. 11*a* and 11*b*). Examining the micro-CT axial sections also showed the newly formed dentin-like structure to be porous and with low density. The newly formed structure did not occupy the entire cross-section of the pulp chamber, and radiolucent porosities, or tunnel defects, were observed at every level from which the newly formed structure was identified. The newly formed structure was not consistent in form and shape. One tooth showed a tunnel defect that was evident under high magnification. The pulp appeared normal with minimal inflammatory cells. The newly formed structure exhibited few odontoblast lacunae but did not bear resemblance to secondary dentin in either form, thickness, organization, or structure. Thickness of the newly formed dentin-like structure was 0.3±0.084 mm when measured histologically and 0.29±0.091 mm when measured by micro-CT (Table 2). The newly formed structure was classified as repair.

Group 2: MTA+EMD

Figure 12:
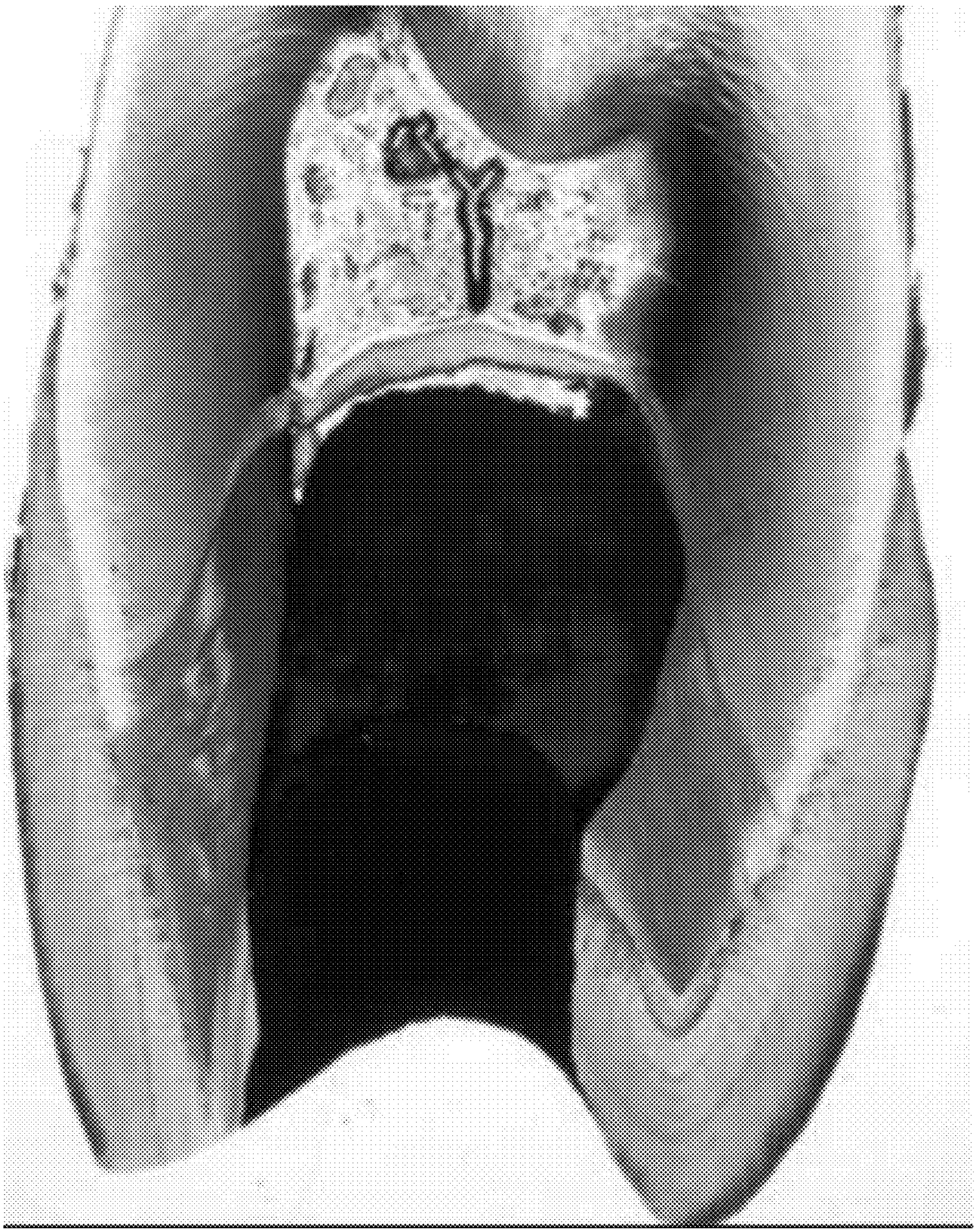
FIG. 12 depicts a histologic section from light microscopy of a tooth extracted 4 months after being pulp capped with MTA+EMD showing uniform and highly dense newly formed dentin-like structure with consistent thickness. Original magnification ×4.

A thick, newly formed dentin-like structure was noted at the 4-month follow-up following application of MTA+EMD ( ) Examining serial axial micro-CT sections showed hard tissue formation from the most coronal to the most apical part of the newly formed structure. Axial views at all cross sections showed the structure to be nonporous. Histologic analyses showed consistent and continuous thickness of the dentin-like structure forming beneath the amalgam and over the pulp tissue, associated with significant root canal obliterations (FIG. 12). No tunnel defects could be seen. Additionally, abundant odontoblast lacunae were present. In all specimens, the pulp tissue appeared normal and the newly formed dentin-like structure appeared highly dense, nontubular, and nonporous. It did not resemble secondary dentin or reactionary tertiary dentin. The thickness of the newly formed dentin-like structure was 0.87±0.09 mm when measured histologically and 0.81±0.17 mm when measured by micro-CT (Table 2). The newly formed dentin-like structure was classified as repair.

Group 3: MTA+rhPDGF

Figure 13:
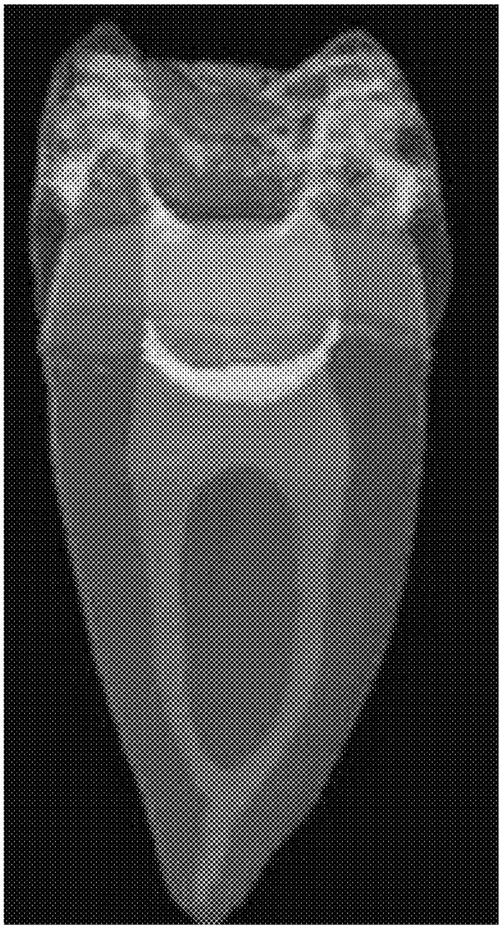
FIG. 13 depicts a color contrasted micro-CT image of a tooth extracted 4 months after being pulp capped with MTA+PDGF showing image evidence of uniform thickness of the newly formed structure sealing the pulpal space (blue=amalgam; red=MTA: orange=newly formed structure).
Figure 14:
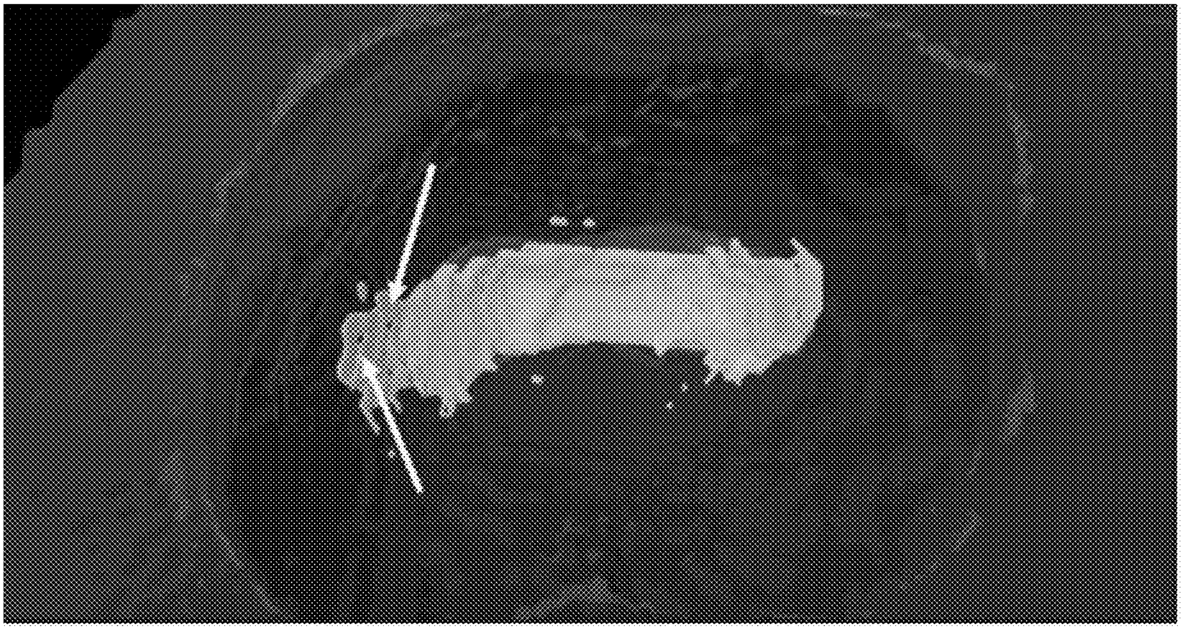
FIG. 14 depicts a color contrasted micro-CT image of the tooth from FIG. 13 in a coronal view showing an uninterrupted, continuous newly formed structure attached to the radicular and coronal dentinal walls. The structure has porosity that resembles secondary dentin (arrows).

The presence of hard tissue apposition was evident at the 4-month follow-up. Sagittal micro-CT images demonstrated complete three-dimensional continuous seal of a thick, newly formed dentin-like structure covering the pulpal space. Contrasted color micro-CT images showed complete continuity of the newly formed structure in the buccolingual and mesiodistal dimensions (FIG. 13). Examining the axial micro-CT sections showed hard tissue formation from the most coronal to the most apical part of the newly formed structure. All micro-CT views confirmed the absence of tunnel defects, presence of normal porosity and thickness of the newly formed structure, patent apices, and absence of root canal obliterations. Abundant odontoblasts lacunae were present in all sides of the newly formed structure. Histologic analysis showed a resemblance of the newly formed dentin-like structure to secondary dentin in porosity, form, and pattern. A reconstructed coronal micro-CT view showed an uninterrupted, continuous newly formed structure attached to the radicular dentinal walls. The structure resembles secondary dentin in its porosity (FIG. 14). Thickness of the newly formed structure was 0.94±0.02 mm when measured histologically and 0.91±0.09 mm when measured by micro-CT (Table 2). The newly formed dentin-like structure was classified as regeneration.

A significant difference in thickness of the newly formed dentin-like structure was found between the MTA group and the other two experimental groups (P<0.05).

TABLE 2

Histomorphometric Analysis, Micro-CT Analysis, and Histologic Findings of the Newly Formed Tissue Thickness over the Pulpal Space

| | Dentin Thickness | | |
|---|---|---|---|
| | Histomorphometric Anaylsis (mm) | Micro-CT Analysis (mm) | Histologic Findings |
| Group 1: MTA | 0.3 ± 0.084 | 0.29 ± 0.091 | The newly formed dentin-like structure had uneven thickness and the pulp tissue exhibited inflammatory infiltrate. The newly formed structure didn't bear resemblance to secondary dentin in either form, thickness, organization, or structure. |
| Group 2: MTA + EMD | 0.87 ± 0.09 | 0.81 ± 0.17 | Newly formed tissues showed consistent and continuous thickness of the dentin-like structure forming beneath the amalgam and over the pulp tissue. It was associated with multiple root canal obliterations without tunnel defects. Abundant odontoblasts lacunae were present. The pulp tissue appeared normal in all specimens. The newly formed dentin-like structure appeared highly dense, nontubular, and nonporous. It did not resemble secondary dentin or reactionary tertiary dentin. |
| Group 3: MTA + rhPDGF | 0.94 ± 0.02 | 0.91 ± 0.09 | Abundant odontoblasts lacunae were present in all sides of the newly formed structure. The newly formed dentin-like structure resembled secondary dentin in porosity, form, and pattern. |

TABLE 2-continued

| Histomorphometric Analysis, Micro-CT Analysis, and Histologic Findings of the Newly Formed Tissue Thickness over the Pulpal Space | | |
|---|---|---|
| Dentin Thickness | | |
| Histomorphometric Anaylsis (mm) | Micro-CT Analysis (mm) | Histologic Findings |
| | | Absence of tunnel defect and complete dentinal bridge sea ling the pulpal space were seen. |

Discussion and Conclusion

A significant difference in the thickness of newly formed dentin-like structure was found between the MTA group and the MTA+EMD and MTA+rhPDGF groups. Regarding the MTA and MTA+EMD groups, histologic, histomorphometric, and micro-CT analyses showed that both groups produced a dentin-like structure that was different in form, density, shape, and thickness from secondary dentin.

The MTA group showed incomplete continuity of dentin-like structure formation. The MTA+rhPDGF group demonstrated abundant and organized odontoblastic lacunae in all dentinal walls. The newly formed structure resembled secondary dentin in pattern, structure, form, shape, porosity, consistent thickness, complete absence of tunnel defects, tissue mineralization, and density. This pattern is different when rhPDGF is used with CaOH2 as a matrix, as shown in Example 1, above. The regenerated dentin in the MTA+rhPDGF group suggests that MTA may be a good matrix to use with rhPDGF. Moreover, it could be that MTA's biocompatibility, sealability, and stability as a matrix during the early stage of wound healing plays a role in this process.

The characteristics of the newly formed dentin-like structure following application of MTA+EMD showed a highly dense structure that was nonporous, without tunnel defects, and with abundant root canal obliterations. The use of MTA as matrix with EMD did not prevent the uncontrolled induction and formation of dentin-like structure. On the other hand, the use of MTA+rhPDGF produced a controlled generation of dentin-like structure with characteristics resembling secondary dentin. This demonstrates that rhPDGF may stimulate and recruit progenitor stem cells to commit to odontoblastic lineage in a more regulated form than EMD.

The findings of the current study can have significant applications for vital pulp therapy. This human randomized clinical trial using rhPDGF+MTA in vital pulp therapy demonstrates the reconstitution of dentin similar to secondary dentin in its form, shape, structural organization, and thickness, while maintaining the pulp integrity. Thus, innovative treatment protocols using rhPDGF together with MTA as a protective biocompatible barrier over exposed pulp tissue to induce dentin regeneration are described herein.

In the present study, two different types of tissue were formed: (1) regenerated dentin-like structure that resembled secondary dentin when rhPDGF+MTA was used; and (2) dentin-like structure that did not resemble secondary dentin when MTA alone or MTA+EMD were used. It appears that both rhPDGF and EMD can increase the thickness of such reparative tissue. Addition of EMD to MTA may increase root canal calcifications.

The results presented in Examples 1 and 2 taken together support that the combination of growth factor substance (e.g., PDGF or EMD) and MTA as the pulp capping material provides superior dentin formation as compared to when calcium hydroxide is used as the pulp capping material.

Particular embodiments of this invention are described herein. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. A number of embodiments of the invention have been described. Nevertheless, it will be understood that various modifications may be made without departing from the spirit and scope of the invention. Accordingly, the descriptions in the Examples section are intended to illustrate but not limit the scope of invention described in the claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A method of pulp capping exposed vital pulp in a tooth, the method comprising:

(a) administering recombinant human platelet-derived growth factor (rhPDGF) directly to exposed vital pulp in a tooth; wherein the rhPDGF is in direct contact with the exposed vital pulp; and (b) placing calcium hydroxide over the rhPDGF administered in step (a);

wherein regenerated dentin is formed in the tooth between the exposed vital pulp and the placed calcium hydroxide.

2. The method of claim 1, wherein the exposed vital pulp is in a cavity in the tooth and the method further comprises: (c) sealing the cavity containing the placed calcium hydroxide with a dental filling.

3. The method of claim 1, wherein the calcium hydroxide is placed to be in contact with dentin at the periphery of the site of exposed vital pulp.

4. The method of claim 1, wherein the rhPDGF is rhPDGF-BB.

5. The method of claim 1, wherein the calcium hydroxide is placed over the rhPDGF administered to the site of exposed vital pulp at least 1 minute, at least 2 minutes, at least 3 minutes, at least 4 minutes, at least 5 minutes, or at least 10 minutes after administering said rhPDGF.

6. The method of claim 1, whereby revitalized pulp tissue occurs in the pulp-capped tooth.

7. The method of claim 1, wherein the exposed vital pulp is normal pulp, pulp having reversible pulpitis, or pulp having irreversible pulpitis.

8. The method of claim 1, wherein the regenerated dentin is secondary dentin.

9. The method of claim 1, wherein the method maintains vitality of the pulp tissue in the tooth, or maintains pulp tissue integrity in the tooth, or a combination thereof.

10. The method of claim 1, wherein the regenerated dentin is formed in the tooth after 3 weeks, after 4 weeks, after 5 weeks, after 6 weeks, after 7 weeks, after 2 months, after 3 months, after 4 months, or after 5 months, following said method.

11. A method of inducing dentin regeneration over exposed vital pulp in a cavity of a tooth, the method comprising:

(a) administering recombinant human platelet-derived growth factor (rhPDGF) directly to exposed vital pulp in a cavity of a tooth; wherein the rhPDGF is in direct contact with the exposed vital pulp;

(b) placing calcium hydroxide over the rhPDGF administered to the exposed vital pulp in step (a), wherein the placed calcium hydroxide is in contact with dentin at a periphery of the site of the exposed vital pulp; and (c) sealing the cavity with a dental filling after step (b);

wherein regenerated dentin is formed in the tooth between the exposed vital pulp and the placed calcium hydroxide.

12. The method of claim 11, wherein the exposed vital pulp is normal pulp, pulp having reversible pulpitis, or pulp having irreversible pulpitis.

13. The method of claim 11, wherein the regenerated dentin is secondary dentin.

14. The method of claim 11, wherein the rhPDGF is rhPDGF-BB.

15. The method of claim 11, wherein the calcium hydroxide is placed over the rhPDGF administered to the site of exposed vital pulp at least 1 minute, at least 2 minutes, at least 3 minutes, at least 4 minutes, at least 5 minutes, or at least 10 minutes after administering said rhPDGF.

16. The method of claim 11, wherein the method revitalizes pulp tissue in the tooth, maintains vitality of the pulp tissue in the tooth, or maintains pulp tissue integrity in the tooth, or combinations thereof.

17. The method of claim 11, wherein the regenerated dentin is formed in the tooth after 3 weeks, after 4 weeks, after 5 weeks, after 6 weeks, after 7 weeks, after 2 months, after 3 months, after 4 months, or after 5 months, following said method.

* * * * *